(12) United States Patent
Sørensen et al.

(10) Patent No.: US 11,311,184 B2
(45) Date of Patent: Apr. 26, 2022

(54) TIP PART FOR A VISION DEVICE

(71) Applicant: AMBU A/S, Ballerup (DK)

(72) Inventors: Morten Sørensen, Ballerup (DK); Thomas Bachgaard Jensen, Copenhagen V (DK); Morten Jacobsen, Hørsholm (DK)

(73) Assignee: AMBU A/S, Ballerup (DK)

( * ) Notice: Subject to any disclaimer, the term of this patent is extended or adjusted under 35 U.S.C. 154(b) by 59 days.

(21) Appl. No.: 16/550,098

(22) Filed: Aug. 23, 2019

(65) Prior Publication Data

US 2020/0060529 A1 Feb. 27, 2020

(30) Foreign Application Priority Data

Aug. 24, 2018 (EP) ..................................... 18190733
Aug. 24, 2018 (EP) ..................................... 18190736

(51) Int. Cl.
*A61B 1/00* (2006.01)
*A61B 1/05* (2006.01)

(52) U.S. Cl.
CPC .......... *A61B 1/051* (2013.01); *A61B 1/00096* (2013.01)

(58) Field of Classification Search
CPC . A61B 1/051; A61B 1/00096; A61B 1/00101; A61B 1/05; A61B 1/0676; G02B 23/2461; G02B 23/2423; H04N 2005/2255
See application file for complete search history.

(56) References Cited

U.S. PATENT DOCUMENTS

| | | | |
|---|---|---|---|
| 4,805,596 A | 2/1989 | Hatori | |
| 5,193,525 A | 3/1993 | Silverstein et al. | |
| 5,718,663 A | 2/1998 | Wulfsberg | |
| 5,879,289 A | 3/1999 | Yarush et al. | |
| 5,993,378 A | 11/1999 | Lemelson | |
| 7,662,094 B2 * | 2/2010 | Iddan ................. | A61B 1/00096 600/176 |

(Continued)

FOREIGN PATENT DOCUMENTS

EP 0 756 845 2/1997
JP H03 264037 11/1991

(Continued)

OTHER PUBLICATIONS

European Search Report in EP 18190736, dated Feb. 11, 2019.
Extended European Search Report in EP18190733.8, dated Feb. 1, 2019.

*Primary Examiner* — Timothy J Neal
(74) *Attorney, Agent, or Firm* — Faegre Drinker Biddle & Reath LLP

(57) ABSTRACT

A tip part for an endoscope has a vision receptor having a vision sensor for providing an image from received light; a first light source; an exterior housing; and a first lens positioned in front of the first light source so that a portion of light emitted from the first light source travels towards and propagates through the first lens; the exterior housing comprising a window consisting essentially of a transparent material, so that light emitted from the first light source can pass through the window to the exterior, the window comprising an exterior surface positioned at in front of the first light source, wherein the first lens is a convex lens and has a convex lens surface integrally provided on an interior surface of the window.

20 Claims, 8 Drawing Sheets

(56) References Cited

U.S. PATENT DOCUMENTS

| | | |
|---|---|---|
| 8,414,480 B2 | 4/2013 | Kendale et al. |
| 8,485,966 B2 | 7/2013 | Robertson |
| 8,790,250 B2 | 7/2014 | Petersen et al. |
| 9,220,400 B2 | 12/2015 | Petersen |
| 9,521,942 B2 | 12/2016 | Robertson |
| 9,622,649 B2 | 4/2017 | Lin |
| 9,854,962 B2 | 1/2018 | McGrail et al. |
| 10,245,402 B2 | 4/2019 | Daher et al. |
| 10,321,804 B2 | 6/2019 | Jacobsen et al. |
| 2004/0064018 A1 | 4/2004 | Dunki-Jacobs et al. |
| 2004/0199052 A1 | 10/2004 | Banik et al. |
| 2004/0242963 A1 | 12/2004 | Matsumoto et al. |
| 2005/0203341 A1 | 9/2005 | Welker et al. |
| 2008/0242935 A1 | 10/2008 | Inoue |
| 2009/0054728 A1 | 2/2009 | Trusty |
| 2009/0177040 A1 | 7/2009 | Lyons et al. |
| 2009/0209819 A1 | 8/2009 | Kitagawa et al. |
| 2010/0286475 A1* | 11/2010 | Robertson .......... A61B 1/00096 600/104 |
| 2011/0118549 A1 | 5/2011 | Han |
| 2011/0245617 A1 | 10/2011 | Kitano |
| 2012/0323078 A1 | 12/2012 | Kikumori et al. |
| 2013/0175720 A1 | 7/2013 | Otsuka et al. |
| 2013/0271588 A1 | 10/2013 | Kirma et al. |
| 2014/0081085 A1 | 3/2014 | Takato et al. |
| 2015/0335227 A1 | 11/2015 | Jacobsen et al. |
| 2016/0106306 A1 | 4/2016 | Furuta |
| 2017/0245734 A1 | 8/2017 | Kaneko |
| 2018/0132700 A1* | 5/2018 | Ouyang ............. A61B 1/00135 |
| 2018/0143421 A1 | 5/2018 | Hegenbarth et al. |
| 2018/0310890 A1 | 11/2018 | Li |
| 2019/0175007 A1 | 6/2019 | Sørensen et al. |

FOREIGN PATENT DOCUMENTS

| | | |
|---|---|---|
| JP | 2004-016455 | 1/2004 |
| JP | 3764512 | 4/2006 |
| JP | 2009-125528 | 6/2009 |
| JP | 2010169802 | 8/2010 |
| JP | 2013009896 | 1/2013 |
| JP | 2018015250 | 2/2018 |
| WO | WO 2005/023099 | 3/2005 |
| WO | WO 2008/115575 | 9/2008 |
| WO | WO 2010/066789 | 6/2010 |
| WO | WO 2010/129324 | 11/2010 |
| WO | WO 2016/188537 | 12/2016 |
| WO | WO 2016/188538 | 12/2016 |
| WO | WO 2016/188539 | 12/2016 |
| WO | WO 2016/188540 | 12/2016 |
| WO | WO 2016/188541 | 12/2016 |
| WO | WO 2016/188542 | 12/2016 |

* cited by examiner

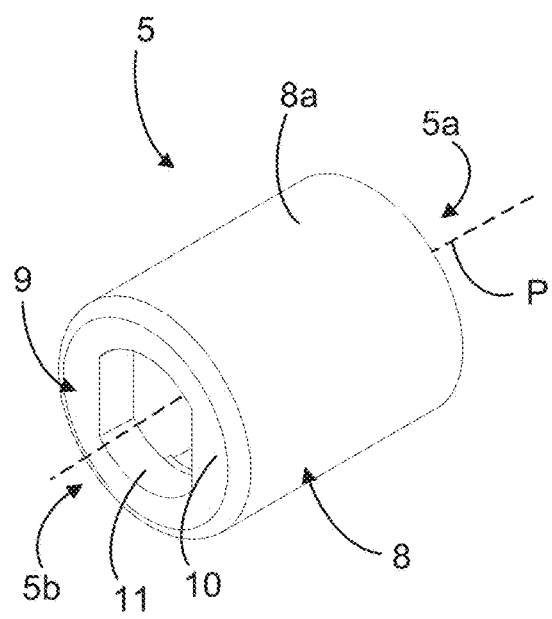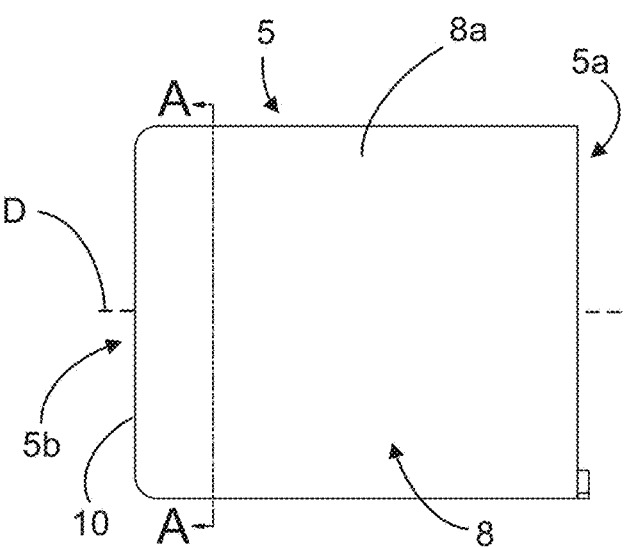
Fig. 6a  Fig. 6b
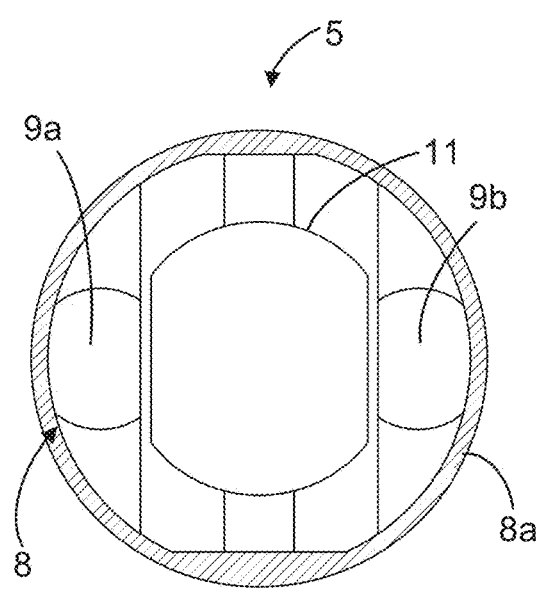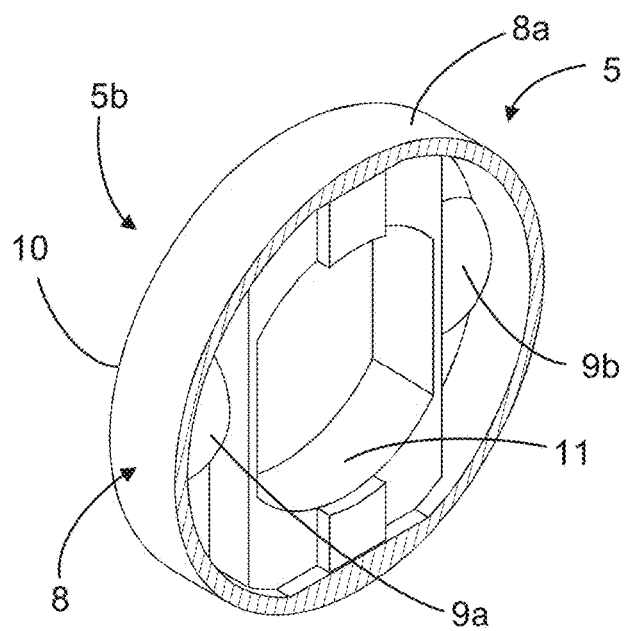
Fig. 6c  Fig. 6d

TIP PART FOR A VISION DEVICE

CROSS-REFERENCE TO RELATED APPLICATIONS

This application claims priority from European Patent Application No. 18190736, filed on Aug. 24, 2018 and from European Patent Application No. 18190733, filed on Aug. 24, 2018, both of which are incorporated herein by reference thereto.

FIELD OF THE DISCLOSURE

The present disclosure relates to vision devices such as but not limited to endotracheal tubes and endoscopes, more specifically to a tip part of such a vision device and a vision device such as an endoscope with such a tip part.

BACKGROUND

Vision devices such as endoscopes are well known for visually inspecting inaccessible places such as human body cavities. Typically, the endoscope comprises an elongated insertion tube with a handle at the proximal end, as seen from the operator, and visual inspection means, such as a built-in camera, at the distal end of the elongated insertion tube. This definition of the terms distal and proximal, i.e. proximal being the end closest to the operator and distal being the end remote from the operator, as used herein for endoscopes in general, is adhered to in the present specification. Electrical wiring for the camera and other electronics, such as LED lighting accommodated in the tip part at the distal end, run along the inside of the elongated insertion tube from the handle to the tip part. Instead of using cameras, endoscopes may also be fiberoptic, in which case the optical fibres run along the inside of the elongated insertion tube to the tip part. A working or suction channel may run along the inside of the insertion tube from the handle to the tip part, e.g. allowing liquid to be removed from the body cavity or allowing for insertion of surgical instruments or the like, into the body cavity. The suction channel may be connected to a suction connector, typically positioned at a handle at the proximal end of the insertion tube.

In order to be able to manoeuvre the endoscope inside the body cavity, the distal end of the endoscope may comprise a bending section with increased flexibility, e.g. a number of articulated segments of which the tip part forms the most distal segment. The maneuvering of the endoscope inside the body is typically done by tensioning or slacking pull wires also running along the inside of the elongated insertion tube from the tip part through the remainder of articulated segments to a control mechanism of the handle.

As the name indicates, endoscopes are used for seeing inside things, such as lungs or other human body cavities of a patient. Modern endoscopes are therefore typically equipped with a light source and a vision receptor including a vision sensor, such as a camera or an image sensor. Provided that sufficient light is present, it is possible for the operator to see where the endoscope is steered and to set the target of interest once the tip has been advanced thereto. This therefore normally requires illumination of the area in front of the distal tip of the endoscope, in particular the field of vision of the camera(s). The light source, such as a light emitting diode or an optical fibre, may provide illumination.

The illumination from the light source may result in an undesirable distribution of light, such as overexposure of the sides of the field of vision and underexposure of the centre of the field of vision, leading to poor vision quality.

One drawback is that prior art tip parts for endoscopes are generally limited to a fixed set of applications. In some new contemplated applications, investigating narrow and hard-to-reach body cavities are necessary. This requires a miniaturisation of the tip part.

Additionally, when, as in some of the embodiments of the present disclosure, the tip part is also intended for use in a disposable endoscope, reducing the manufacturing and assembly costs of the tip part are important.

Additionally, when, as in some of the embodiments of the present disclosure, the insertion tube of the endoscope is intended to be inserted into a human body cavity, the insertion tube furthermore needs to be sealed in a watertight manner. This is in particular the case for the distal tip part as it accommodates the camera, LED(s) and other delicate electronics, prone to malfunction or destruction if exposed to humidity.

On this background, it may be seen as an object of the present disclosure to provide a tip part mitigating at least some of the above drawbacks.

One or more of these objects may be met by the present disclosure as described in the following.

SUMMARY OF THE DISCLOSURE

A tip part for an endoscope and an endoscope including the tip part are provided. A first aspect of the disclosure relates to a tip part for an endoscope. In some embodiments, the tip part comprises a vision receptor having a vision sensor for providing an image from light received from an object to be investigated; a first light source; an exterior housing accommodating the vision receptor and the light source; a proximal or back end for connection to another part of the endoscope, such as an insertion tube of the endoscope; a distal or front end for receiving light from the object; and a first lens positioned in front of the first light source so that a portion of light emitted from the first light source travels towards and propagates through the first lens; the exterior housing comprising a window positioned at the distal end, the window consisting essentially of a translucent or a transparent material, so that light emitted from the first light source can pass through the window to the exterior, the window comprising an exterior surface positioned at least partly in front of the first light source, wherein the first lens is a convex lens and has a convex lens surface integrally provided on an interior surface of the window.

By integrating the first lens in the window, manufacturing and assembly costs may be reduced since fewer parts are to be produced and assembled. Additionally, an integral provision of the first lens may allow a well-defined positioning of the lens, which further reduces the complexity of assembly and manufacture. Furthermore, this may allow provision of a miniaturised tip part as the window in conjunction with the exterior housing, provides water tightness also provides the optical advantages of a lens. This may also ensure that an optical axis of the first lens is aligned with an optical axis of the vision receptor, which may ensure that the light source provides adequate illumination for the vision receptor.

Additionally or alternatively, the convex lens surface of the first lens may be a convex interior lens surface. The first lens may be a first plano-convex lens. The convex lens surface of the first lens may be a convexly curved lens surface. The convex lens surface of the first lens may form part of a backwardly directed protrusion integrally provided on an interior surface of the window. The light source or light sources may be a light emitting diode(s).

A second aspect of the disclosure relates to a tip part for an endoscope. In some embodiments, the tip part comprises a vision receptor having a vision sensor for providing an image from light received from an object to be investigated; a first light source; an exterior housing accommodating the vision receptor and the light source; a proximal or back end for connection to another part of the endoscope, such as an insertion tube of the endoscope; a distal or front end for receiving light from the object; and a first lens positioned in front of the first light source so that a portion of light emitted from the first light source travels towards and propagates through the first lens; the exterior housing integrally comprising a window positioned at the distal end, the window consisting essentially of a translucent or a transparent material, and so that light emitted from the first light source can pass through the window to the exterior, the window comprising an exterior surface positioned at least partly in front of the first light source, wherein the first lens has a lens surface integrally provided on an interior surface of the window, and wherein the exterior housing is a moulded part at least partially, potentially completely, encasing the vision receptor.

By integrating the first lens in the window, manufacturing and assembly costs may be reduced since fewer parts are to be produced and assembled. Additionally, an integral provision of the first lens may allow a well-defined positioning of the lens, which further reduces the complexity of assembly and manufacture. Furthermore, this may allow provision of a miniaturised tip part as the window in conjunction with the exterior housing, provides water tightness also provides the optical advantages of a lens. This may also ensure that an optical axis of the first lens is aligned with an optical axis of the vision receptor, which may ensure that the light source provides adequate illumination for the vision receptor. Further, this may provide the advantage that water tightness of the tip part is ensured while the complex process of assembling separate lenses inside the exterior housing is avoided.

Additionally or alternatively, the lens surface of the first lens may be an interior lens surface.

Additionally or alternatively, the first lens may be a first convex lens, potentially a first plano-convex lens. The convex lens surface of the first lens may be a convexly curved lens surface. The lens surface of the first lens may form part of a backwardly directed protrusion integrally provided on an interior surface of the window. The light source or light sources may be a light emitting diode(s).

Additionally or alternatively, the first lens may be a first concave lens, potentially a first plano-concave lens. The lens surface of the first lens may be a concave lens surface, potentially a concavely curved lens surface. The lens surface of the first lens may form part of a depression integrally provided on an interior surface of the window. The light source or light sources may be a light fibre(s) or laser(s).

The following additional or alternative features may apply to any one of the first and second aspect of the present disclosure.

The exterior housing may further comprise an exterior side wall. The exterior side wall may extend from the distal end of the tip part to the proximal end of the tip part. The exterior side wall may extend from the window. The exterior side wall may extend along sides of the vision receptor and first light source. The exterior side wall may have a substantially cylindrical shell shape. The exterior side wall and window may be integrally formed. The exterior housing, potentially the exterior side wall of the exterior housing, may form a barrier or border between the exterior of the tip part and the interior of tip part. The exterior housing may define an internal volume, in which the vision receptor and the light source are positioned. The exterior housing may accommodate a working channel for supplying fluid to the distal end of the tip part, a printed circuit board of the vision receptor, and/or the vision sensor of the vision receptor. The exterior housing may essentially consist of the same material as the window.

Additionally or alternatively, the light source or light sources may be a light fibre(s) and/or a light emitting diode(s) and/or a laser(s).

The tip part may comprise a second light source. The second light source may be provided similarly as the first light source. The second light source may be positioned on an opposite side of the vision receptor in relation to the first light source.

The vision sensor of the vision receptor may be an image sensor, such as a camera. The vision receptor may comprise a vision lens or a plurality of vision lenses potentially arranged successively and optionally in the casing. The vision receptor may comprise a printed circuit board for converting light received by the vision receptor to an image. The exterior housing may accommodate the printed circuit board.

The plurality of vision lenses may be arranged in front of the vision sensor, potentially so that an optical axis of the vision lens, potentially of the plurality of vision lenses, align or coincide with an optical axis of the vision sensor. The plurality of vision lenses may be spaced by at least one spacer, potentially a plurality of spacers. The vision lens or the plurality of vision lenses may be chosen to provide suitable optical characteristics for the vision sensor. The type of the vision lens or the plurality of vision lenses may be selected from the group consisting of: plano-concave, plano-convex, bi-concave, bi-convex, positive meniscus, negative meniscus, fresnel, wafer, or any other suitable lens type.

The lens surface may be a first or interior lens surface of the first lens. The first lens may comprise a second or exterior lens surface provided on an exterior surface of the window. The second lens surface may be provided on an opposite side of the window. The second lens surface may be positioned directly in front of the first lens surface. An optical axis of the first lens surface may be aligned or coincide with an optical axis of the second lens surface. The second lens surface may be plane, convex or concave. An optical axis of the first lens may be aligned, potentially be coinciding, with an optical axis of the first light source and/or an optical axis of the vision receptor. Additionally or alternatively, the first lens may be a first housing lens or a first interior lens, and/or the second lens may be a second housing lens or a second interior lens.

The tip part may comprise a working tube potentially forming part of the working channel of the endoscope. The exterior housing may accommodate the working tube. The working tube may be sealed in relation to the exterior housing, potentially so that fluid in the working tube may not ingress into the interior of the exterior housing.

Additionally or alternatively, the window and the first lens may be integrally formed or being in one piece.

Additionally or alternatively, the exterior housing may integrally comprise the window. The window forms part of the exterior housing. The window may be a cap for the exterior housing.

Additionally or alternatively, the window is positioned at a distal end of the tip part.

Additionally or alternatively, the window is not positioned at least partly in front of the vision receptor. The vision receptor, potentially a lens barrel of the vision receptor, may be attached and sealed to the window, potentially by an adhesive. The window may comprise an opening, in which the vision receptor may be positioned. A gap between the window and the vision receptor may be sealed by an adhesive.

Additionally or alternatively, the window may be a front window, potentially allowing the vision receptor to receive image information from the front of the tip part. The exterior surface of the window may be an exterior front surface.

Additionally or alternatively, the window may be a side window, for instance when the endoscope is a duodenum endoscope. The side window may allow the vision receptor to receive image information from a side, potentially from a radial direction, of the tip part. The exterior surface of the window may be an exterior side surface.

Additionally or alternatively, the window may comprise a front window and a side window.

A translucent material may be defined as a material that allows light, potentially visible light, to propagate therethrough, but not necessarily detailed shapes. The translucent material may be a polymer, glass, plastic polymer, or any other suitable material, e.g. silicone.

Additionally or alternatively, the window may comprise, potentially consist essentially of, a transparent material. A transparent material will be able to transmit some image information and may potentially be defined as allowing at least 50% of light entering the window at the exterior surface to pass through the window. A transparent material will be able to transmit more image detail than a translucent material. The transparent material may be a polymer, glass, plastic polymer, or any other suitable material, e.g. silicone.

In this specification, a lens may be defined as a device with curved surfaces having the ability to focus, collimate, or disperse light propagating through curved surfaces of the lens.

In this specification, a lens effect may be defined as a lens' ability to alter properties of light propagating there through, such as focusing, collimating, or dispersing light.

In this specification, an optical axis may be defined as a line along which there is some degree of rotational symmetry in an optical system, such as a lens and/or vision sensor.

In this specification, the term "in front of" when referring to the position of an element relative to an optical device, such as a lens, a vision receptor, and/or a light source, the element may be understood to be positioned so that the optical device has an optical effect on the element. For instance, a lens positioned in front of a light source may be understood so that the lens is positioned so that light emitted from the light source propagates directly through the lens.

In this specification, the term "to accommodate" may additionally or alternatively be defined as "to house" or "to enclose" or "to surround". For instance, the exterior housing may enclose or surround the vision receptor and/or the light source.

In this specification, the terms "integrally" or "integrally provided" or "integrally comprising" or similar may be defined as the associated features forms an integral part of a whole; and/or being moulded in one piece; and/or being substantially inseparable by hand.

In this specification, the term "proximal" may be defined as being closest to the operator and the term "distal" as being remote from the operator. The term "proximal-distal axis" may be defined as an axis extending between these two extremes, in the present case the proximal-distal axis may be a centre axis of the tip part extending between a proximal extremity of the proximal end of the tip part and a distal extremity of the distal end of the tip part. A front part of the tip part may be distally oriented and a back or rear part of the tip part may be proximally oriented.

In this specification, the distal end of the tip part should not be construed to only comprise the most distal extremity of the tip part, rather the term "distal end of the tip part" should be understood as a portion of the tip part being distally positioned, e.g. a remaining portion of the tip part relative to the proximal or back end and/or a portion of the tip part for not being connected to other parts of the endoscope and/or a distally located half of the tip part. In some embodiments, the window may be a side window positioned at the distal or front end of the tip part.

In this specification, the term "interior" may be defined as being positioned in an interior space of the tip part, and the term "exterior" may be defined as being positioned in an exterior space of the tip part or as not being positioned in an interior space of the tip part.

In this specification, an endoscope may be defined as a device adapted for viewing bodily cavities and/or channels of a human and/or animal body. The endoscope may for instance be a conventional flexible or steerable endoscope, an endotracheal tube potentially provided with a camera and light source for ensuring the correct position of the endotracheal tube, for instance a laryngoscope. The tip part may additionally or alternatively be for a medical vision device, such as an endoscope.

Additionally or alternatively, the exterior surface of the window may be positioned at least partly in front of the vision receptor so that light received from the object can pass through the window to the vision receptor, the window may consist essentially of an transparent material.

By positioning the exterior surface of the window in front of the vision receptor and the light source, the water tightness of the tip part may be further improved as fewer sealing is required. Additionally, the assembly and/or manufacturing costs may be reduced.

Additionally or alternatively, the exterior housing may further comprise an exterior side wall extending from the window along sides of the vision receptor and the first light source, the exterior side wall and window may be integrally formed or being in one piece.

By providing an exterior side wall integrally with the window, the water tightness of the tip part may be further improved as fewer sealing is required. Additionally, the assembly and/or manufacturing costs may be reduced.

Additionally or alternatively, the exterior surface may be substantially planar, potentially having no lens effect.

By having a planar exterior surface, it may be ensured that the surface does not provide a lens effect even if the physical phase of the investigated material in front of the window changes, for instance between water and air. This may ensure consistent optical performance of the first lens with different types of material on the exterior side of the first lens. Additionally, a plane exterior surface may have an added benefit of improved hygiene as matter, for instance bodily matter, may not stick well to the plane surface.

Additionally or alternatively, an exterior surface of the first lens is substantially planar. Additionally or alternatively, the first lens may be a first plano-convex lens having two lens surfaces, wherein the first lens surface is provided by the convexly curved surface integrally provided on the interior surface of the window and the second lens surface is provided by a portion of the planar exterior surface.

The term "substantially planar" may be defined as plane within a tolerance of 0.5 mm, 0.4 mm, 0.3 mm, 0.2 mm, or preferably 0.1 mm.

Additionally or alternatively, the lens surface of the first lens is an interior lens surface being integrally provided on the interior surface of the window, wherein the first lens may comprise an exterior lens surface integrally provided on the exterior surface and positioned in front of, potentially directly in front of, the interior lens surface.

By having an exterior lens surface, the optical characteristics of the lens may be further customised to the application of the tip part. In particular, a first lens of this kind may enable a stronger lens effect, i.e. a shorter focal length.

Additionally or alternatively, the first lens is a biconvex lens comprising the interior lens surface and the exterior lens surface, wherein the interior lens surface is convexly curved and the exterior lens surface is convexly curved. The exterior lens surface may form part of a forwardly directed protrusion integrally provided on the exterior surface of the window. The forwardly direction protrusion may be positioned on a directly opposite side of the window in relation to the backwardly directed protrusion of the first lens.

Additionally or alternatively, the first lens may form part of a collar positioned in the exterior housing at the distal end, wherein the collar may maintain a position of the vision receptor relative to the exterior housing.

This may provide the advantage that the positioning of the vision receptor relative to the first lens is more well-defined. Furthermore, this may ease the assembly of the tip part as the collar provides a tactile insertion of the vision receptor into the exterior housing.

The collar may at least partly surround the vision receptor. The collar may define an insertion space for the vision receptor. The collar may comprise a wall partly surrounding the vision receptor, and the first lens may comprise a recess forming part of the wall. The vision receptor may be attached to the collar potentially by glue.

Additionally or alternatively, the tip part comprises a substantially planar mounting surface positioned between the first lens and the first light source, so as to maintain the position of the first light source in relation to the first lens.

This may improve the assembly of the tip part as the light source is easier to assemble into the exterior housing.

Additionally or alternatively, the first light source may abut, be fixed to, be mounted on, and/or be glued to the mounting surface.

Additionally or alternatively, the tip part may comprise a first optical trap or a first optical well of the transparent material positioned between the first light source and the vision receptor so that a portion of light emitted from the first light source and reflected from the exterior surface enters the first optical well, whereby stray light is at least partially prevented from entering the vision receptor.

Additionally or alternatively, first optical trap or the optical well may be a backwardly directed protrusion or an interior protrusion. The window may integrally comprise the first optical trap or first optical well.

The first optical well may be positioned so that a portion of stray light from the first light source, being internally reflected in the window, is redirected into the first optical well, whereby the portion of stray light may be internally reflected in the first optical well away from the vision receptor; absorbed in the first optical well, potentially by a light absorbing material surrounding the first optical well, such as a partly, substantially completely opaque, and/or black material; and/or refracted out of the first optical well away from the vision receptor.

A material may be provided surrounding the first optical well. The material may be air; gas; solid; light absorbing, such as partly or substantially completely opaque.

Additionally or alternatively, the first optical well may be formed as a ridge between the first light source and the vision receptor.

In this specification, stray light may be defined as light emitted from a light source, which ingresses into a vision receptor before being reflected by an outside or investigated object, for instance by internal reflections in the window. This may cause unwanted optical artefacts in the image produced by the vision receptor.

Additionally or alternatively, the window comprises, potentially consists essentially of, a first material and the exterior housing comprises, potentially consists essentially of, a second, different material, the window and exterior housing being integrally formed potentially by a two component moulding process.

This may provide the advantage that the exterior housing and window can be made of materials more suited to their requirements, for instance the exterior housing may be made of an opaque material and the window may be made of a translucent or a transparent material.

The first material may be a first polymer material, potentially a first translucent or transparent polymer material. The second material may be a second, different polymer material, potentially a second opaque polymer material. The window and exterior housing may be integrally formed in one piece by a two component moulding process.

Additionally or alternatively, an endoscope may comprise a tip part according to the first aspect of the present disclosure. The endoscope may comprise an elongated insertion tube with a handle at the proximal end. The tip part may be positioned at the distal end of the elongated insertion tube. The tip part may further comprise a bending section positioned between the tip part and the elongated insertion tube. The bending section may be configured to articulated, so as to manoeuvre the endoscope inside a body cavity.

A person skilled in the art will appreciate that any one or more of the above aspects of the present disclosure and embodiments thereof may be combined with any one or more of the other aspects of the present disclosure and embodiments thereof.

BRIEF DESCRIPTION OF DRAWINGS

The present disclosure will now be described in greater detail based on non-limiting exemplary embodiments and with reference to the drawings, on which:

FIG. 6a shows an isometric view of a second embodiment of a tip part according to the present disclosure, FIG. 6b shows a side view of the second embodiment and a cross-sectional line A-A, FIG. 6c shows a rear view of a cross-section along the line A-A of FIG. 6b as seen from the proximal end 5a of the tip part 5, FIG. 6d shows an isometric view of a cross-section along the line A-A of FIG. 6b.

DETAILED DESCRIPTION

Figure 1A:
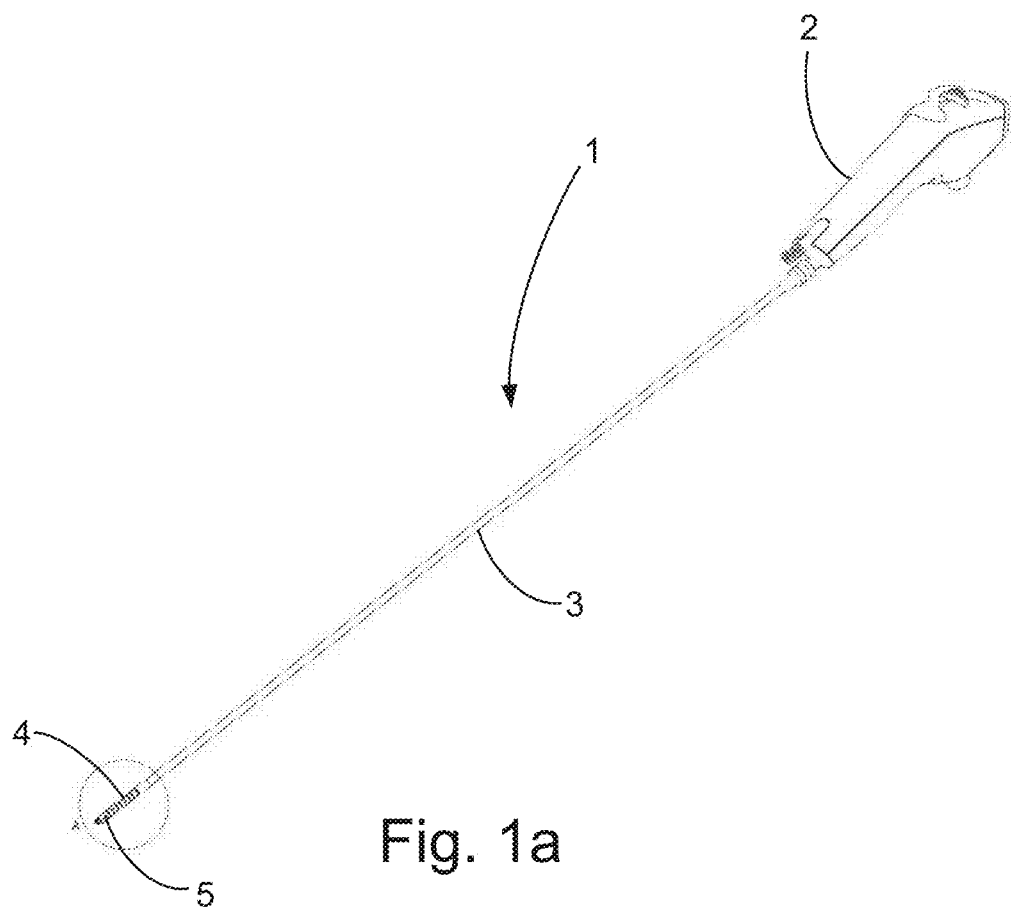
FIG. 1a shows an isometric view of an endoscope in which a tip part according to an embodiment of the present disclosure is implemented.

Turning first to FIG. 1a, an endoscope 1 exemplifying the vision device according to the present disclosure is shown. The endoscope 1 comprises a handle 2 at the proximal end of the endoscope 1, an insertion tube 3 extending towards the distal end of the endoscope 1 where it comprises an articulated bending section 4, which as the most distal segment has a distal tip part 5 according to the present disclosure. Though omitted for illustration purposes the articulated bending section 4 will normally be covered by a suitable sleeve, connected at least at its own distal end to the distal tip part 5, e.g. by means of an adhesive. The tip part 5 of the present disclosure is intended as a tip part 5 for a disposable endoscope 1 to be thrown away after use and low manufacturing costs is therefore an important issue.

Figure 1B:
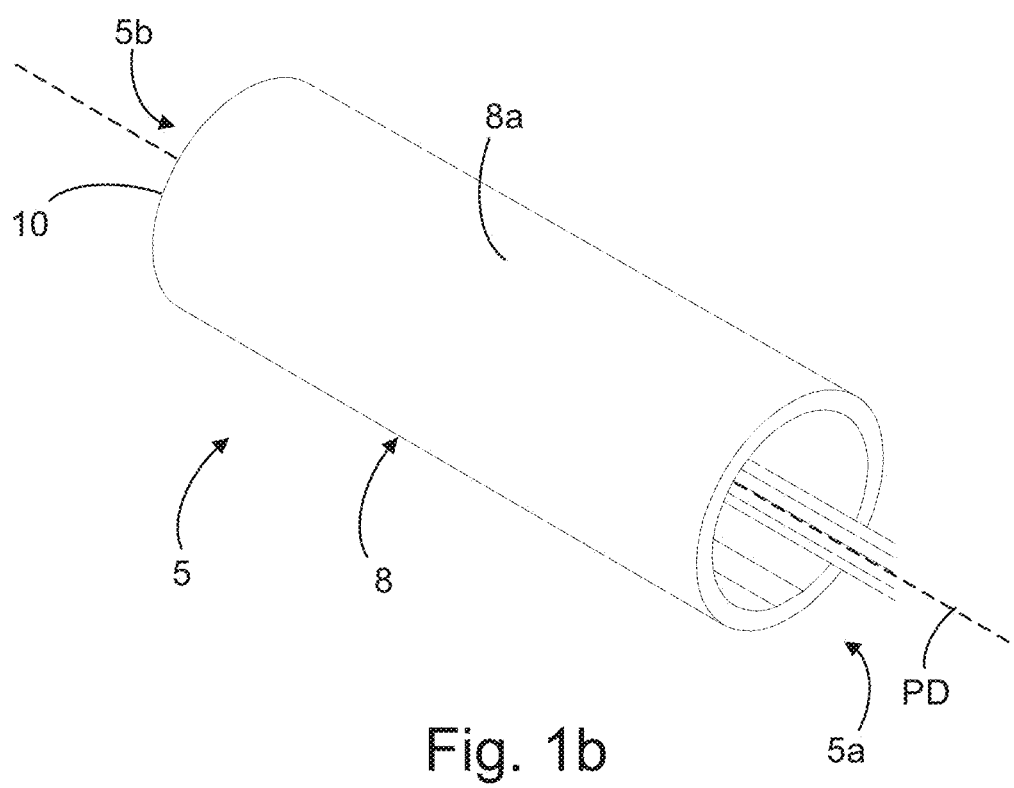
FIG. 1b shows an isometric view of a first embodiment of a tip part according to the present disclosure.

In FIG. 1b, a first embodiment of a tip part 5 is shown. The tip part 5 is configured to be incorporated in the endoscope shown in FIG. 1a. The tip part 5 has a proximal end 5a for connection to the insertion tube 3 of endoscope 1 and a distal end 5b for receiving light from an object (not shown) located in front of the tip part 5. The tip part 5 further comprises an exterior housing 8 including an exterior surface 10 positioned at the distal end 5b of the tip part 5, and an exterior side wall 8a extending along a proximal-distal axis PD of the tip part 5 between the proximal end 5a and the distal end 5b. The wall 8a and exterior surface 10 are integrally formed in a one-piece construction. The exterior housing 8 forms a barrier between the exterior of the tip part 5 and the interior of tip part 5. The exterior side wall 8a has a substantially cylindrical shell shape with the proximal-distal axis PD coinciding with a centre of the cylindrical shell shape of the exterior side wall 8a.

Figure 2A:
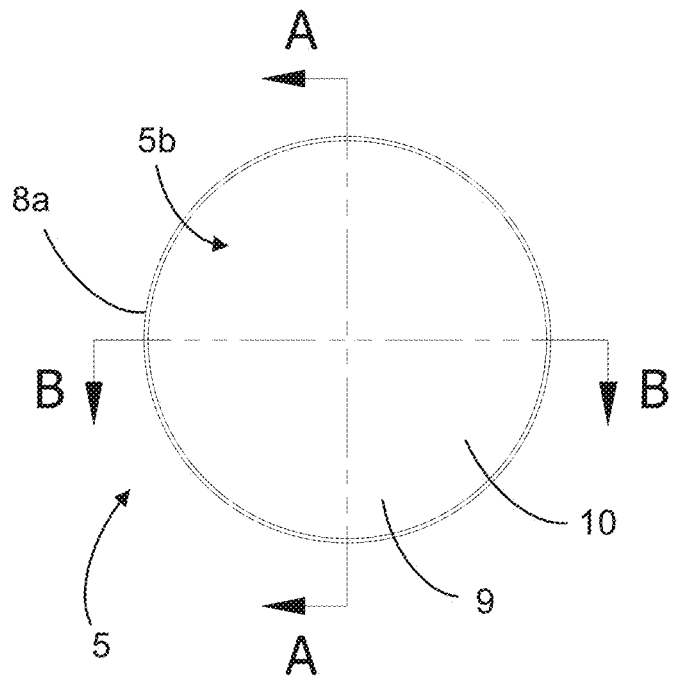
FIG. 2a shows a front view of a distal end of the tip part of FIG. 1b and cross-sectional lines A-A, B-B.
Figure 2B:
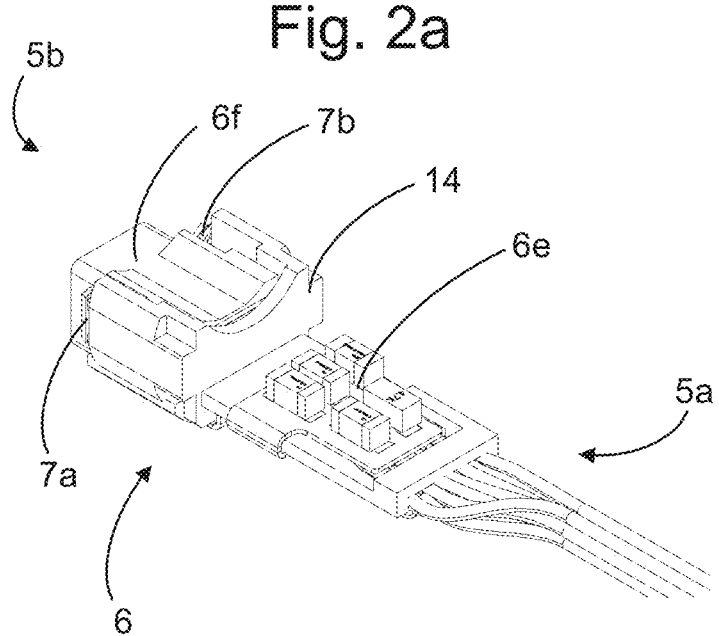
FIG. 2b shows an isometric view of a vision receptor of the first embodiment.

Turning to FIG. 2a, the tip part 5 comprises a window 9 formed integrally with the exterior housing 8 by a two component moulding process, wherein the exterior housing is moulded firstly and the window 9 is moulded secondly. The window 9 is positioned with an exterior surface 10 at the distal end 5b of the tip part 5. Behind the window 9 is a vision receptor 6 shown in more detail in FIG. 2b.

The vision receptor 6 comprises an interior housing 14 which supports a casing 6f having an image sensor 6a and a first vision lens 6b arranged in the casing 6f. The interior housing 14 further supports a first light source 7a (see FIG. 2b) and a second light source 7b (see FIG. 2b) in the form of light emitting diodes and a printed circuit board 6e for converting light received by the image sensor 6a to an image. The light sources 7a, 7b are positioned on opposite sides of the casing 6f. Cables connect the printed circuit board 6e to the remaining parts of the endoscope 1 for allowing transfer of the image captured by the vision receptor 6 to a viewing device (not shown) for visually presenting the image to an operator of the endoscope 1.

As best seen in FIGS. 3a, 3b, 4a and 4b, the window 9 consists essentially of a transparent polymer, so that light emitted from the light sources 7a, 7b can pass through the window 9 to the exterior. The window 9 comprises a first lens 9a and a second lens 9b positioned directly in front of the light sources 7a, 7b source, so that a portion of light emitted from the light sources 7a, 7b travels towards and propagates through the associated lens 9a, 9b. The lenses 9a, 9b are plano-convex lenses and each has a convexly curved lens surface integrally provided on an interior surface of the window 9 and a planar lens surface forming part of the exterior surface 10. The convexly curved lens surface forms part of a backwardly directed protrusion of the window 9.

Figure 3A:
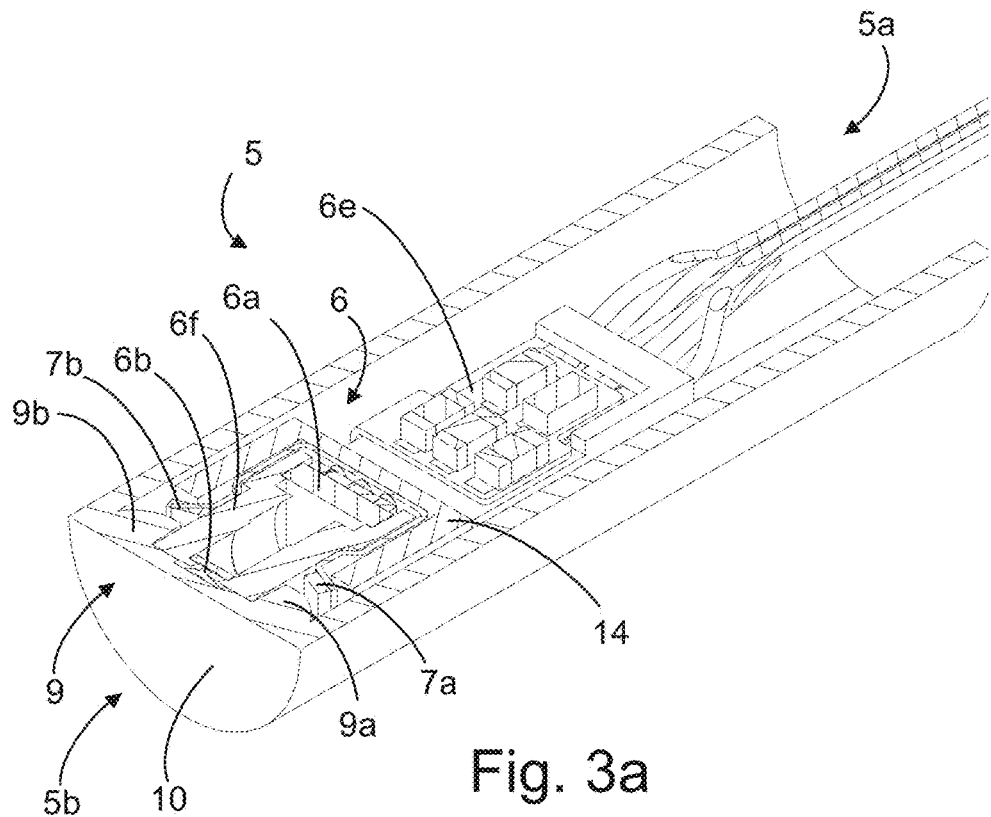
FIG. 3a shows an isometric view of a cross-sectional view of the tip part of FIG. 2a along the line A-A.
Figure 3B:
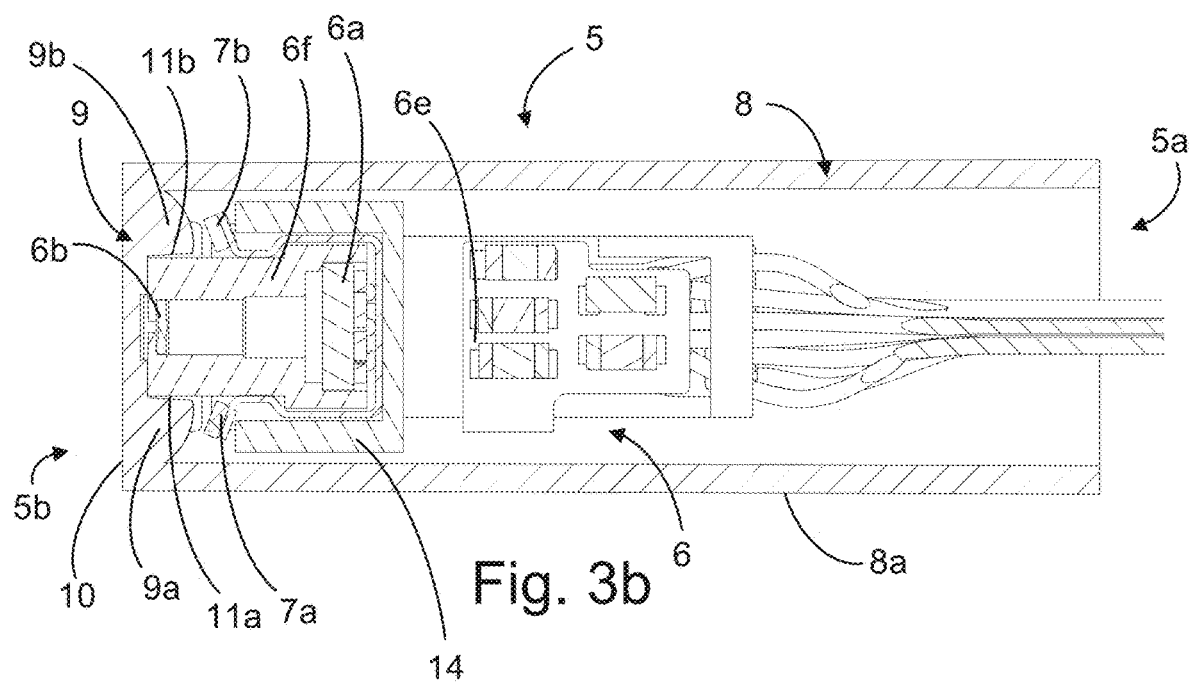
FIG. 3b shows a side view of a cross-sectional view of the tip part along the line A-A of FIG. 2a, FIG. 4a shows an isometric view of a cross-sectional view of the tip part along the line B-B of FIG. 2a, FIG. 4b shows a side view of a cross-sectional view of the tip part along the line B-B of FIG. 2a, FIG. 5a shows a side view of the first embodiment of the tip part with hidden lines shown as dashed lines.
Figure 4A:
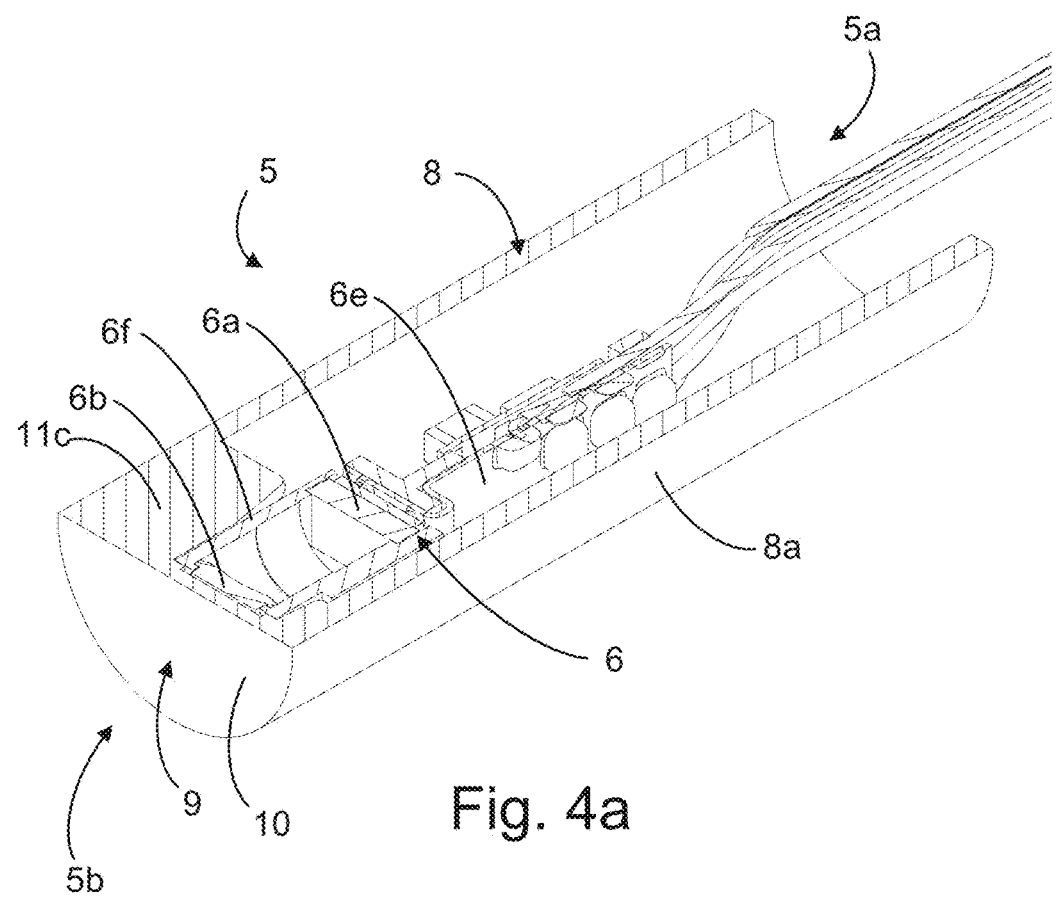
Figure 4B:
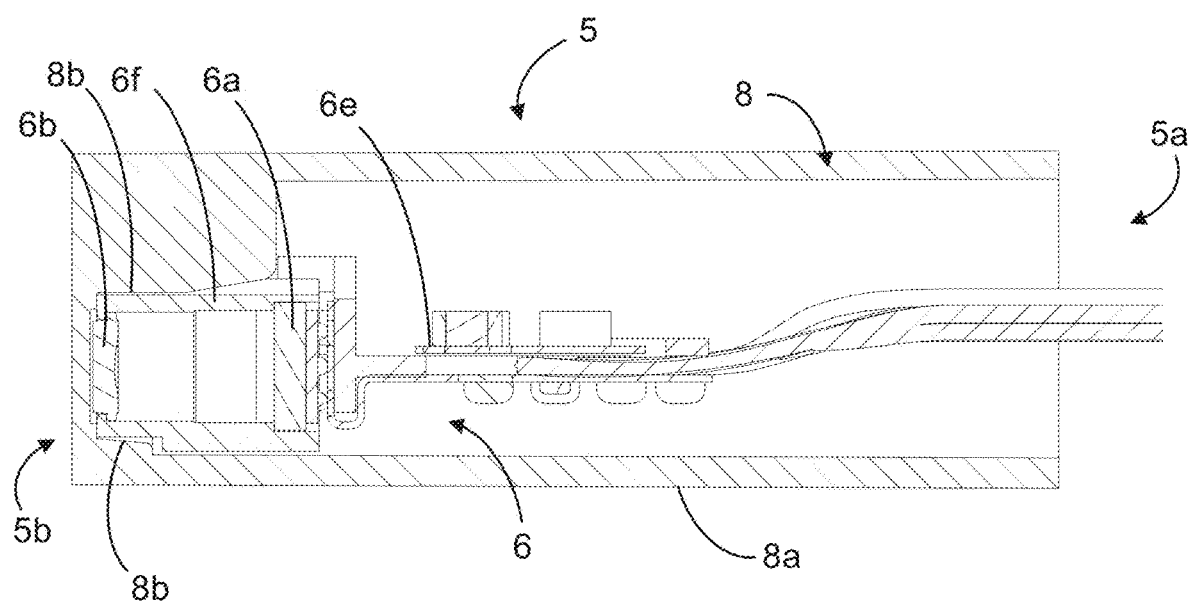
Figure 5A:
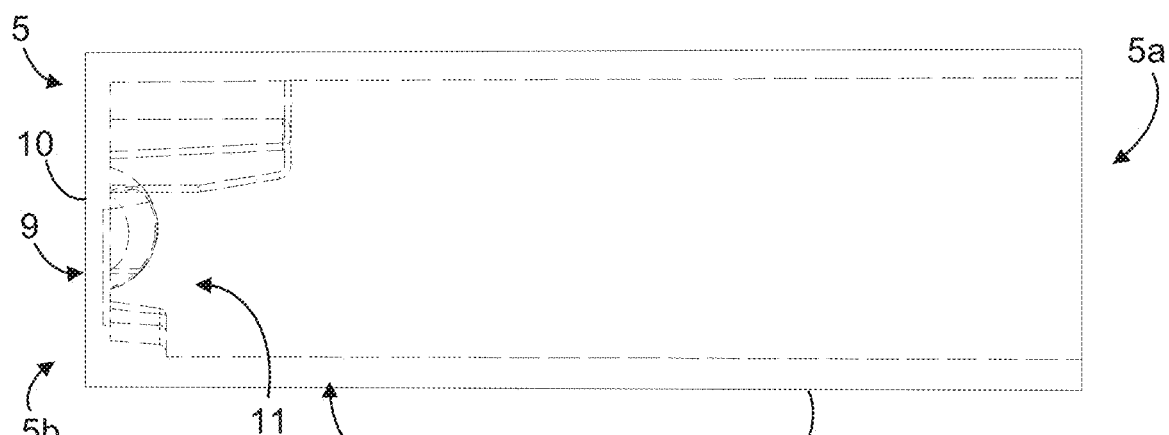
FIG. 5b shows an isometric view of a cross-sectional view of the tip part along a centre line of FIG. 5a, FIG. 5c shows a rear view of the tip part of FIG. 5a as seen from the proximal end 5a of the tip part 5.
Figure 5B:
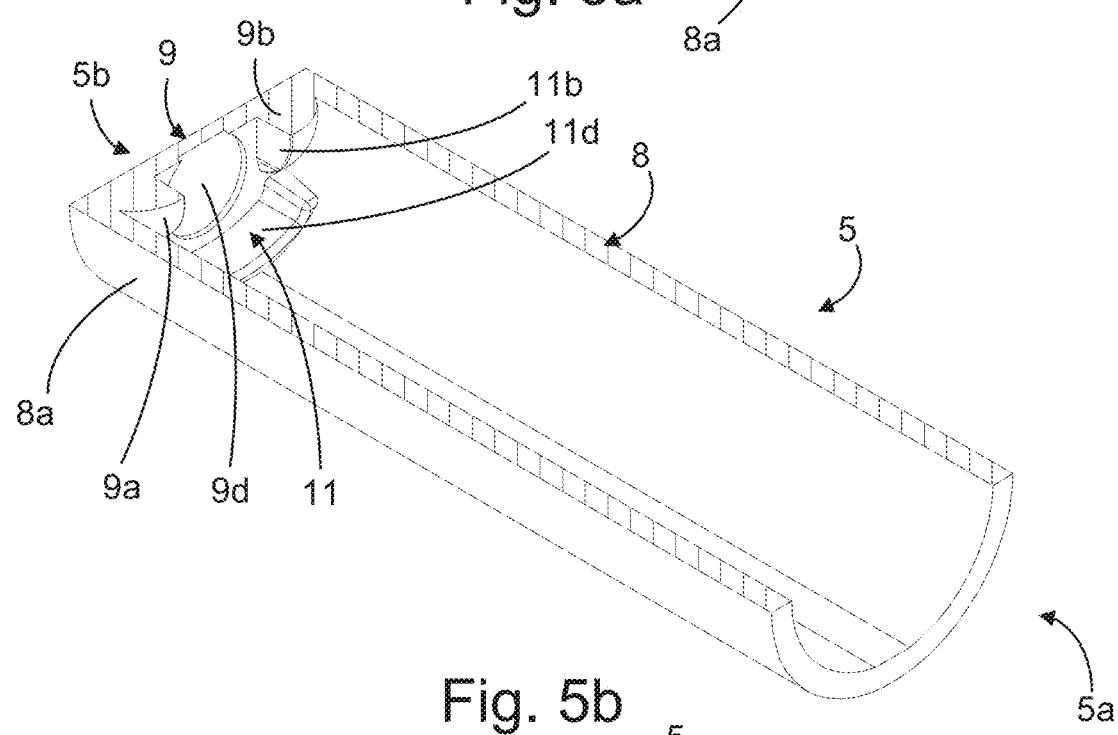
Figure 5C:
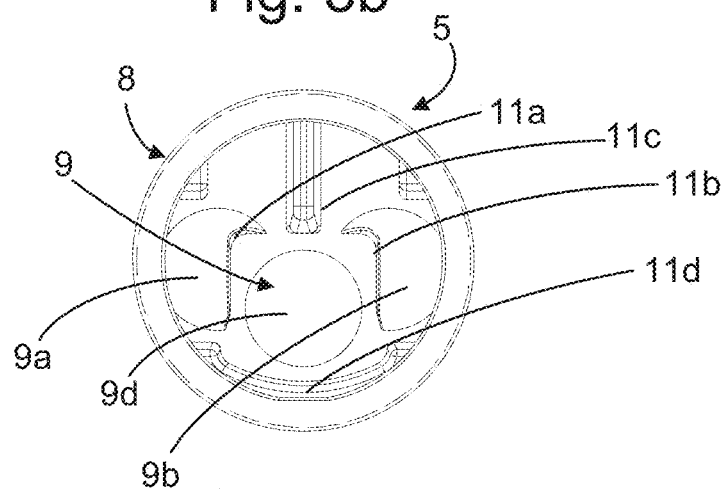

Turning to FIGS. 5a, 5b, and 5c, the exterior housing 8 comprises a collar 11 positioned inside the exterior housing 8 at the distal end 5b. The collar 11 maintains the position of the vision receptor 6 relative to the exterior housing 8. The lenses 9a, 9b form part of the collar 11 each maintaining the position of a different corner of the casing 6f, as best seen in FIG. 3b. The collar 11 further comprises a holder 11d maintaining the position of the remaining two corners of the casing 6f. Additionally, the collar 11 has a rib 11c supporting the casing 6f, as best seen in FIG. 4b.

In FIGS. 6a, 6b, 6c, and 6d, an exterior housing 8 of a second embodiment of a tip part 5 is shown. In this embodiment, the window 9 does not cover the front of the vision receptor 6. Instead, the exterior surface 10 comprises an opening at the distal end forming a collar 11 for inserting the vision receptor 6 into and positioning the vision receptor 6 flush with the exterior surface 10. The collar 11 maintains the position of the vision receptor 6. The lenses 9a, 9b are positioned between the exterior side wall 8a and the collar 11.

Figure 7A:
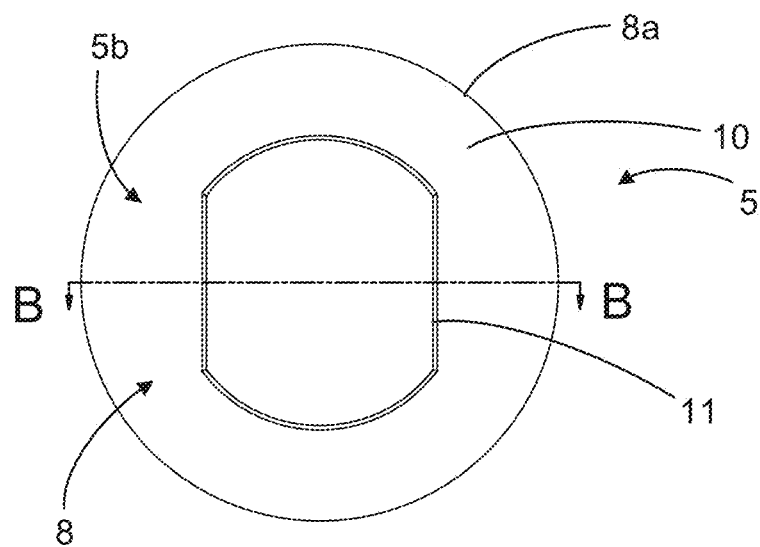
FIG. 7a shows a front view of the second embodiment.
Figure 7B:
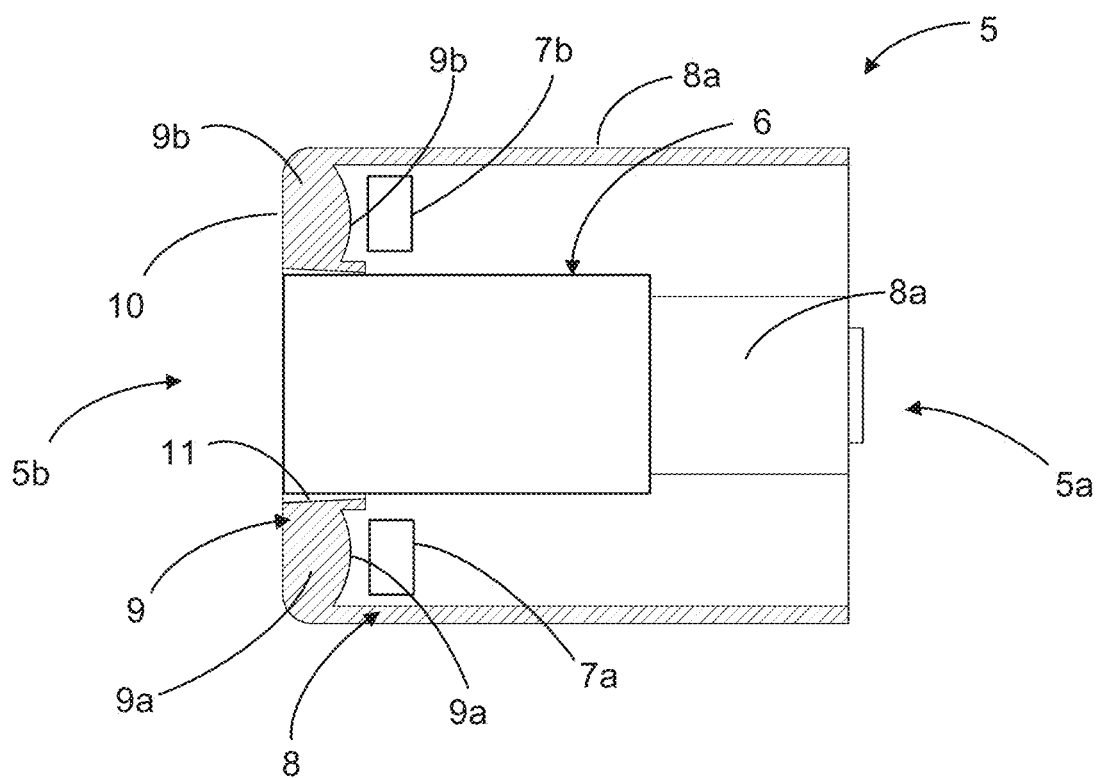
FIG. 7b shows a side view of a cross-section along the lines B-B of FIG. 7a, FIG. 8 shows a schematic side view of a cross-section of a third embodiment, the cross-section is similar to the one shown in FIG. 7b.

Turning to FIGS. 7a and 7b, the position of the vision receptor 6 is shown. The vision receptor 6 can be connected to the remaining parts of the endoscope 1 for allowing viewing of the image captured by the vision receptor 6. The vision receptor can be sealed to the collar 11 by means of an adhesive (not shown) so as to form a water tight tip part 5. The light sources 7a, 7b in the form of LEDs are positioned behind the associated lens 9a, 9b and aligned so that light emitted by the light sources 7a, 7b propagate through the lenses 9a, 9b.

Figure 8:
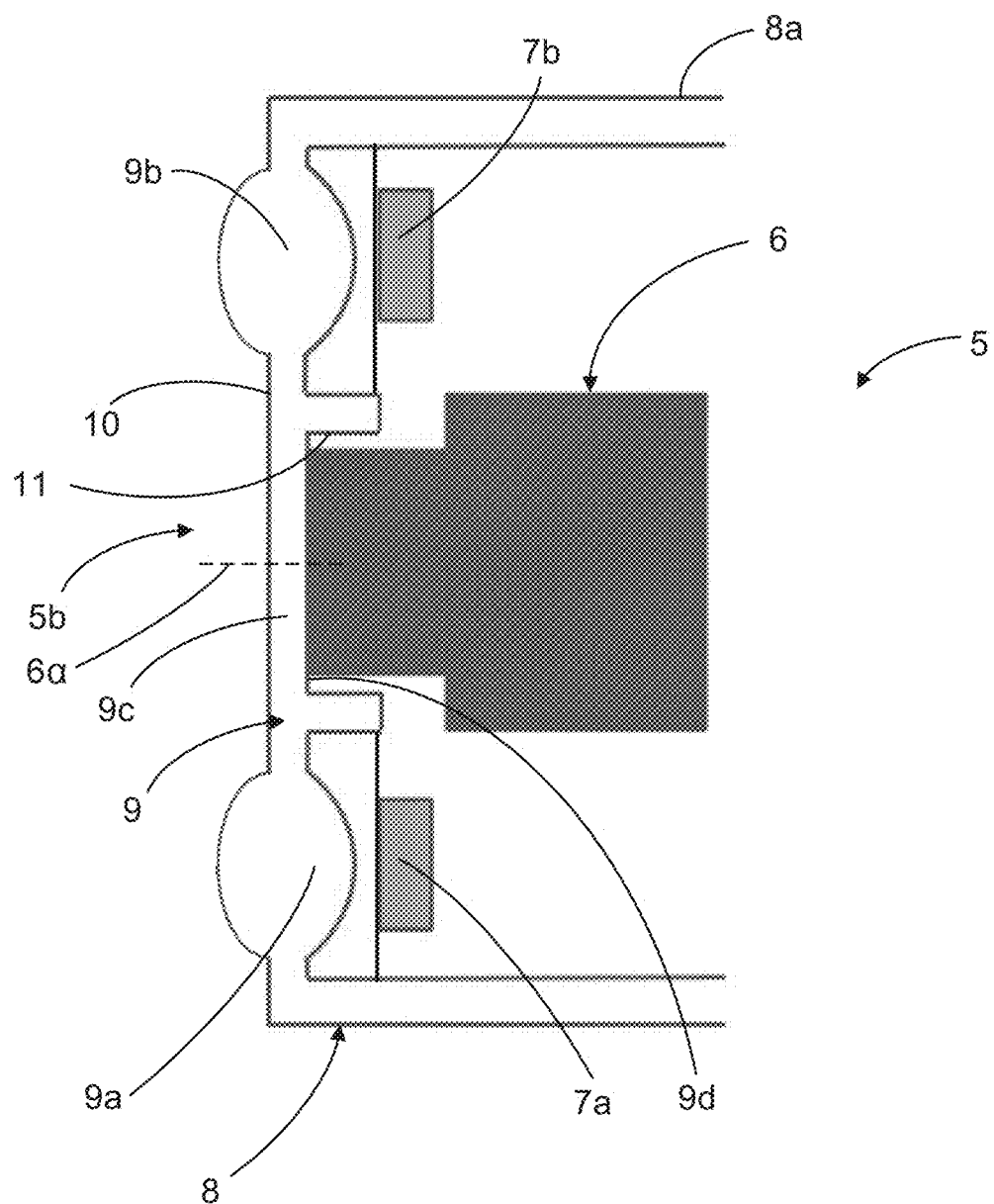

In FIG. 8, a third embodiment of a tip part 5 is shown. The window 9 of the tip part 5 covers the light sources 7a, 7b and the vision receptor 6 forming a water tight tip part 5. In this embodiment, the lenses 9a, 9b do not form part of the collar 11. The collar 11 is formed by a backwardly directed protrusion provided integrally on the interior surface of the window 9. The backwardly directed protrusion also functions as a first optical trap or a first optical well of the transparent material positioned between the first light source and the vision receptor so that a portion of light emitted from the first light source and reflected from the exterior surface enters the first optical well, whereby stray light is at least partially prevented from entering the vision receptor. The backwardly directed protrusions extend proximally past a most-distal end of the vision receptor and may be radially spaced apart from the convex lens to thereby form light wells that prevent at least some stray light emitted by the first light source from reflecting from the window and entering into the vision receptor. The optical well, or trap, may improve the image quality of the vision receptor by allowing the stray light being internally reflected in the window to pass through the end of the optical well, where it does not affect the optical performance of the vision receptor.

The first optical well and/or second optical well may have a width measured in a substantially outwardly direction, potentially a radial direction, less than 1 mm, 0.9 mm, 0.8 mm, 0.7 mm, 0.6 mm, 0.5 mm, 0.4 mm, 0.3 mm, or 0.25 mm.

The outwardly direction may be a radial direction of the tip part, potentially orthogonal to the proximal-distal axis. When the optical well is a ridge the width may be the width of the ridge.

Additionally or alternatively, the first optical well and/or second optical well may have a depth and a width, the depth may be at least 1 times, 1.5 times, 2 times, or 3 times greater than the width, the width may be measured in a substantially outwardly direction, potentially a radial direction of the tip part, the depth may be measured in the proximal-distal direction, potentially an axial direction of the tip part.

Additionally or alternatively, a distance normal to the optical axis of the light source between the associated convex lens and the associated optical well is 10%, 20%, 30%, 40%, 50%, 60%, 70%, 75%, 80%, 90%, or 100% of the width of the associated optical well.

Additionally or alternatively, a distance between the optical axis of the light source and the associated optical well may be 1 times, 2 times, 3 times, 4 times, or 5 times the width of the associated optical well, the distance may be normal to the optical axis of the light source.

The lenses 9a, 9b are bi-convex lenses and each has a convexly curved interior lens surface integrally provided on an interior surface of the window 9 and a convexly curved exterior lens surface integrally provided on the exterior surface 10. The exterior housing 8 comprises two planar mounting surfaces positioned adjacent each lens 9a, 9b. Each mounting surface is positioned between the associated lens 9a, 9b and the associated light source 7a, 7b. The light sources 7a, 7b are glued to the associated mounting surface to maintain the position of the light sources 7a, 7b in relation to the lenses 9a, 9b.

As described above, to assemble the tip part, a front part comprising the exterior side wall and the window (including the first and second lens) is provided. An electronics assembly is then assembled including the circuit board, the interior housing, and the vision receptor. The circuit board is wrapped around the interior housing (best seen in FIG. 4b and the vision sensor is connected to the circuit board. The electronics assembly is then inserted through the proximal end of the exterior side wall of the exterior housing until the casing fits in the collar. The casing may abut the window to minimize stray light entry therefrom. The casing may be press-fit or bonded in or to the collar or the window.

LIST OF REFERENCES

The following is a list of reference numerals used throughout this specification.
1 endoscope
2 handle
3 insertion tube
4 bending section
5 tip part
5a proximal end
5b distal end
6 vision receptor
6a vision sensor
6b vision lens
6d spacer
6e printed circuit board
6f holder
6α optical axis of vision receptor
7a first light source
7b second light source
8 exterior housing
8a exterior side wall
8b collar
8c rib
9 window
9a first lens
9b second lens
9c vision receptor zone
9d abutment surface
10 exterior surface
11 collar
11a first lens recess
11b second lens recess
11c rib
11d holder
13 tube
14 interior housing
PD proximal-distal axis

We claim:

1. A tip part for an endoscope, the tip part comprising:
a vision receptor having a vision sensor for providing an image from light received from an object to be investigated;
a first light source;
an exterior housing having a proximal end and a distal end, the exterior housing accommodating the vision receptor and the light source and comprising a window positioned at the distal end of the exterior housing, the window comprising an exterior surface positioned at least partly in front of the first light source and at least partly in front of the vision receptor; and
a first lens positioned in front of the first light source so that a portion of light emitted from the first light source travels towards and propagates through the first lens, wherein the first lens is a convex lens and has a convex lens surface extending proximally from the window.

2. The tip part of claim 1, wherein the convex lens surface of the first lens is integrally provided in one-piece with the window, and wherein the exterior housing is a moulded part at least partially encasing the vision receptor.

3. The tip part of claim 2, wherein the exterior housing is a moulded part completely encasing the vision receptor, and wherein the exterior housing is a moulded part formed in one-piece with the window and the first lens.

4. The tip part of claim 1, wherein the exterior housing comprises an exterior side wall extending from the window, the exterior side wall and the window being integrally formed in one piece.

5. The tip part of claim 1, wherein the exterior surface of the window is substantially planar.

6. The tip part of claim 1, wherein the convex lens surface of the first lens is an interior convex lens surface being integrally provided on the interior surface of the window, and wherein the first lens comprises an exterior convex lens surface integrally provided on the exterior surface of the window and positioned in front of the interior convex lens surface.

7. The tip part of claim 1, wherein the first lens forms part of a collar positioned in the exterior housing at the distal end, wherein the collar maintains a position of the vision receptor relative to the exterior housing.

8. The tip part of claim 1, wherein the tip part comprises a substantially planar mounting surface positioned between the first lens and the first light source, so as to maintain the position of the first light source in relation to the first lens.

9. The tip part of claim 1, wherein the tip part comprises a first optical trap or a first optical well of a transparent material positioned between the first light source and the vision receptor so that a portion of light emitted from the first light source and reflected from the exterior surface enters the first optical well, whereby stray light is at least partially prevented from entering the vision receptor.

10. The tip part of claim 1, wherein the window comprises a first material and the exterior housing comprises a second material, the second material being different than the first material, the window and exterior housing being integrally formed by a two component moulding process.

11. An endoscope, comprising: a tip part according to claim 1.

12. A tip for an endoscope, comprising:
a first light source;
an external housing having a proximal end spaced apart from a distal end, the external housing including a window positioned at the distal end and a wall extending from the proximal end to the distal end, the wall and an interior surface of the window defining an interior of the housing, the interior surface of the window in front of the first light source having a convex shape extending proximally from the window and forming a convex lens; and
a vision receptor supported within the interior of the housing, the vision receptor including a casing and a vision sensor.

13. The tip of claim 12, wherein the window of the housing covers the vision receptor.

14. The tip of claim 12, wherein an exterior surface of the window in front of the vision sensor is substantially planar.

15. The tip of claim 14, wherein an exterior surface of the window in front of the first light source has a convex shape.

16. The tip of claim 12, wherein the vision receptor penetrates through an opening in the window and a most-distal surface of the vision receptor is flush with an exterior surface of the window.

17. The tip of claim 12, wherein the window includes a collar extending into the interior of the housing, the collar supporting the vision receptor at the distal end of the housing.

18. The tip of claim 17, wherein the collar comprises at least two backwardly directed protrusions extending from the window intermediate the convex lens and the vision receptor.

19. The tip of claim 18, wherein the at least two backwardly directed protrusions extend proximally past a most-distal end of the vision receptor and are radially spaced apart from the convex lens to thereby form light wells that prevent at least some stray light emitted by the first light source from reflecting from the window and entering into the vision receptor.

20. The tip of claim 19, wherein an exterior surface of the window in front of the first light source has a convex shape.

* * * * *